United States Patent [19]
Williams et al.

[11] Patent Number: 5,840,300
[45] Date of Patent: Nov. 24, 1998

[54] METHODS AND COMPOSITIONS COMPRISING SINGLE CHAIN RECOMBINANT ANTIBODIES

[75] Inventors: William V. Williams, Havertown; David B. Weiner, Merion Station, both of Pa.

[73] Assignee: Trustees of the University of Pennsylvania, Philadelphia, Pa.

[21] Appl. No.: 526,583

[22] Filed: Sep. 11, 1995

[51] Int. Cl.[6] ........................ A61K 39/395; A61K 39/42; A61K 38/00; C07H 21/02

[52] U.S. Cl. .................................... 424/135.1; 424/148.1; 530/324; 530/325; 530/326; 530/388.35; 536/23.1

[58] Field of Search .............................. 424/135.1, 148.1; 530/388.35, 324, 325, 326; 536/23.1

[56] References Cited

PUBLICATIONS

Barbas III, C. et al., "Human Monoclonal Fab Fragments Derived from a Combinatorial Library Bind to Respiratory Syncytial Virus F Glycoprotein and Neutralize Infectivity", *PNAS USA* 1992, 89, 10164–10168.

Barbas III, C. et al., "Assembly of Combinatorial Antibody Libraries on Phage Surfaces: The Gene III Site", *PNAS USA* 1991, 88, 7978–7982.

Barbas III, C. et al., "Recombinant Human Fab Fragments Neutralize Human Type 1 Immunodficiency Virus in vitro", *PNAS USA* 1992, 89, 9339–9343.

Better, M. et al., "*Escherichia coli* Secretion of an Active Chimeric Antibody Fragment", *Science* 1988, 240, 1041–1043.

Bird, R. et al., "Single–Chain Antigen–Binding Proteins", *Science* 1988, 242, 423–426.

Blanche, S. et al., "A Prospective Study of Infants Born to Women Seropositive for Human Immunodeficiency Virus Type 1", *The New England J. of Medicine* 1989, 320 (25), 1643–1648.

Brinkmann, U. et al., "A Recombinant Immunotoxin Continuing a Disulfide–Stabilizing Fv Fragment", *PNAS USA* 1993, 90, 7538–7542.

Burton, D. et al., "A Large Array of Human Monoclonal Antibodies to Type 1 Human Immunodficiency Virus from Combinatorial Libraries of Asymptomatic Seropositive Individuals", *PNAS USA* 1991, 88, 10134–10137.

Calvelli, T. and Rubinstein, "Intravenous Gamma–Globulin in Infant Acquired Immunodficiency Syndrome", *Pediatric Infectious Disease* 1986, 5 (3), S207–210.

Crowe, J.S. et al., "Improved Cloning Efficiency of Polymerase Chain Reaction (PCR) Products After Proteinase K Digestion", *Nucleic Acids Res* 1991, 19 (1), 184.

Davis, G. et al., "Single Chain Antibody (SCA) Encoding Genes: One–Step Construction and Expression in Eukaryotic Cells", *Bio/Technology* 1991, 9, 165–169.

Earl, P. et al., "Biological and Immunological Properties of Human Immunodeficiency Virus Type 1 Envelope Glycoprotein: Analysis of Proteins with Truncations and Deletions Expression by Recombinant Vaccinia Viruses", *J. of Virology* 1991, 65 (1), 31–41.

Fiore, J. et al., "Correlation Between Seroreactivity to HIV–1 V3 Loop Peptides and Male–to–Female Heterosexual Transmission", *AIDS* 1993, 7 (1), 29–31.

Goedert, J. et al., "Mother–to–Infant Transmission of Human Immunodficiency Virus Type 1: Association with Prematurity or Low Anti–gp120", *The Lancet* 1989, ii, 1351–1354.

(List continued on next page.)

*Primary Examiner*—Jeffrey Stucker
*Assistant Examiner*—Hankyel T. Park
*Attorney, Agent, or Firm*—Woodcock Washburn Kurtz Mackiewicz & Norris, LLP

[57] ABSTRACT

Methods and compositions for the generation of single chain antibody fragments.

5 Claims, 8 Drawing Sheets

OTHER PUBLICATIONS

Hasemann, C. and Capra, "High–level Production of a Functional Immunoglobulin Heterodimer in a Baculovirus Expression System", *PNAS USA* 1990, 87, 3942–3946.

Horwitz, A. et al., "Secretion of Functional Antibody and Fab Fragment From Yeast Cells", *PNAS USA* 1988, 85, 8678–8682.

Huse, W. et al., "Generation of a Large Combinatorial Library of the Immunoglobulin Repertoire in Phage Lambda", *Science* 1989, 246, 1275–1281.

Kabat, E. et al., "Sequences of Proteins of Immunological Interest", U.S. Department of Health and Human Services, 1991.

Kang, A. et al., "Linkage of Recognition and Replication Functions by Assembling Combinatorial Antibody Fab Libraries Along Phage Surfaces", *PNAS USA* 1991, 88, 4363–4366.

Lindgren, S. et al., "HIV and Child–bearing; Clinical Outcome and Aspects of Mother–to–Infant Transmission", *AIDS* 1991, 5 (9), 1111–1116.

MacDonald, M. et al., "HIV Infection in Pregnancy: Epidemiology and Clinical Management", *J. of IADS* 1991, 4, 100–108.

McCallus, D. et al., "Construction of a Recombinant Bacterial Human CD4 Expression System Producing a Bioactive CD4 Molecule", *Viral Immunology* 1992, 5 (2), 163–172.

Montefiori, D. et al, "Evaluation of Antiviral Drugs and Neutralizing Antibodies to Human Immunodeficiency Virus by a Rapid and Sensitive Microtiter Infection Assay", *J. of Clinical Microbiology* 1988, 26 (2), 231–235.

Nara, P., "Quantitative Infectivity Syncytium–Forming Immunoassay", in Techniques in HIV Research, Aldovini, A. and Walker, eds., Stockton Press, New York, 1989, pp. 77–86.

Newell, M.L. et al., "Risk Factors for Mother–to–Child Transmission of HIV–1", *The Lancet* 1992, 339, 1007–1012.

Osther, K. et al., "Protective Humoral Immune Responses to the Human Immunodeficiency Virus Induced in Immunized Pigs: A Possible Source of Therapeutic Immunoglobulin Preparations", *Hybridoma* 1991, 10 (6), 673–683.

Prince, A. et al., "Prevention of HIV Infection by Passive Immunization with HIV Immunoglobulin", *AIDS Res. and Human Retroviruses* 1991, 7, 971–972.

Putney, S., "How Antibodies Block HIV Infection: Paths to an AIDS Vaccine", *Trends Biochem. Sci. (TIBS)* 1992, 17, 191–196.

Rossi, P. et al., "Presence of Maternal Antibodies to Human Immunodeficiency Virus 1 Envelope Glycoprotein gp120 Epitopes Correlates with the Uninfected Status of Children Born to Seropositive Mothers", *PNAS USA* 1989, 86, 8055–8058.

Saragovi, H. et al., "Design and Synthesis of a Mimetic from an Antibody Complementarity–Determining Region", *Science* 1991, 253, 792–795.

Sarantopoulos, S. et al., "A Method for Linking $V_L$ and $V_H$ Region Genes That Allows Bulk Transfer Between Vectors for Use in Generating Polyclonal IgG Libraries", *J. of Immunology* 1994, 152, 5344–5351.

Scarlatti, G. et al., "Comparison of Variable Region 3 Sequences of Human Immunodeficiency Virus Type 1 from Infected Children With the RNA and DNA Sequences of the Virus Populations of their Mothers", *PNAS USA* 1993, 90,1721–1725.

Skerra, A. and Pluckthun, "Assembly of a Functional Immunoglobulin $F_V$ Fragment in *Escherichia coli*", *Science* 1988, 240, 1038–1041.

Smith, G., "Filamentous Fusion Phage: Novel Expression Vectors That Display Cloned Antigens on the Virion Surface", *Science* 1985, 228, 1315–1317.

Ugen et al., "Ocular Manifestations of HIV–1 Infection", *AIDS Reader* 1994, 4, 66–71.

Ugen, K. et al., "Vertical Transmission of Human Immunodeficiency Virus (HIV) Infection Reactivity of Maternal Sera with Glycoprotein 120 and 41 Peptides from HIV Type 1", *J. Clin. Invest.* 1992, 89, 1923–1930.

Wang, B. et al., "Gene Inoculation Generates Immune Responses Against Human Immunodeficiency Virus Type 1", *PNAS USA* 1993, 90, 4156–4160.

Wang, B. et al., "Molecular Cloning, Expression, and Biological Characterization of an HTLV–II Envelope Glycoprotein: HIV–1 Expression Is Permissive for HTLV–II–Induced Cell Fusion", *AIDS Research and Human Retroviruses* 1993, 9 (9), 849–860.

Williams, W. et al., "Recombinant Single Chain Human Antibodies to HIV–1 gp160", *Transgene* 1993, 1, 113–123.

Williamson, R.A. et al., "Human Monoclonal Antibodies Against a Plethora of Viral Pathogens From Single Combinatorial Libraries", *PNAS USA* 1993, 90, 4141–4145.

Vittecoq et al., Passive immunotherapy in AIDS: A double–blind randomized study based on transfusions of plasma rich in anti–human immunodficiency virus 1 antibodies vs. transfusions of seronegative plasma, Proc. Natl. Acad. Sci., vol. 92, pp. 1195–1199, Feb. 1995.

Ho, Viral Counts Count in HIV Infectio, Science, vol. 272, p1124–1125, entire article, May 1996.

Mellors, et al., Prognosis in HIV–1 Predicted by the Quantity of Virus in Plasma, Science, vol. 272, p. 1167–1170, entire article, May 1996.

Tilley et al., a human monoclonal antibody against the CD4–binding site of HIV–1 gp120 exhibits potent, broadly neutralizing activity, Res. Virol., 142, 247–259, see Abstract, Jul. 1991.

Fahey et al., Status of immune–based therapies in HIV infection and AIDS Clin. Exp. Immunol. (1992) 88, 1–5, Jan. 1992.

Fox, J.L., No winners against AIDS, Bio/Technology, (1994) vol. 12, Feb. p. 128, Feb. 1994.

Robinson et al., Identification of Conserved and Variant Epitopes of Human Immunodeficiency Virus Type 1 (HIV–1) gp120 by Human Monoclonal Antibodies Produced by EBV–Transformed Cell Lines, Aids Research and Human Retroviruses, vol. 6, No. 5, pp. 567–577, See Abstract, May 1990.

Posner et al., An IgG Human Monoclonal Antibody that Reacts with HIV–1/GP120, Inhibits Virus Binding to Cells, and Neutralizes Infection, Journal of Immunology, vol. 146, No. 12, 4325–4332, see Abstract, Jun. 1991.

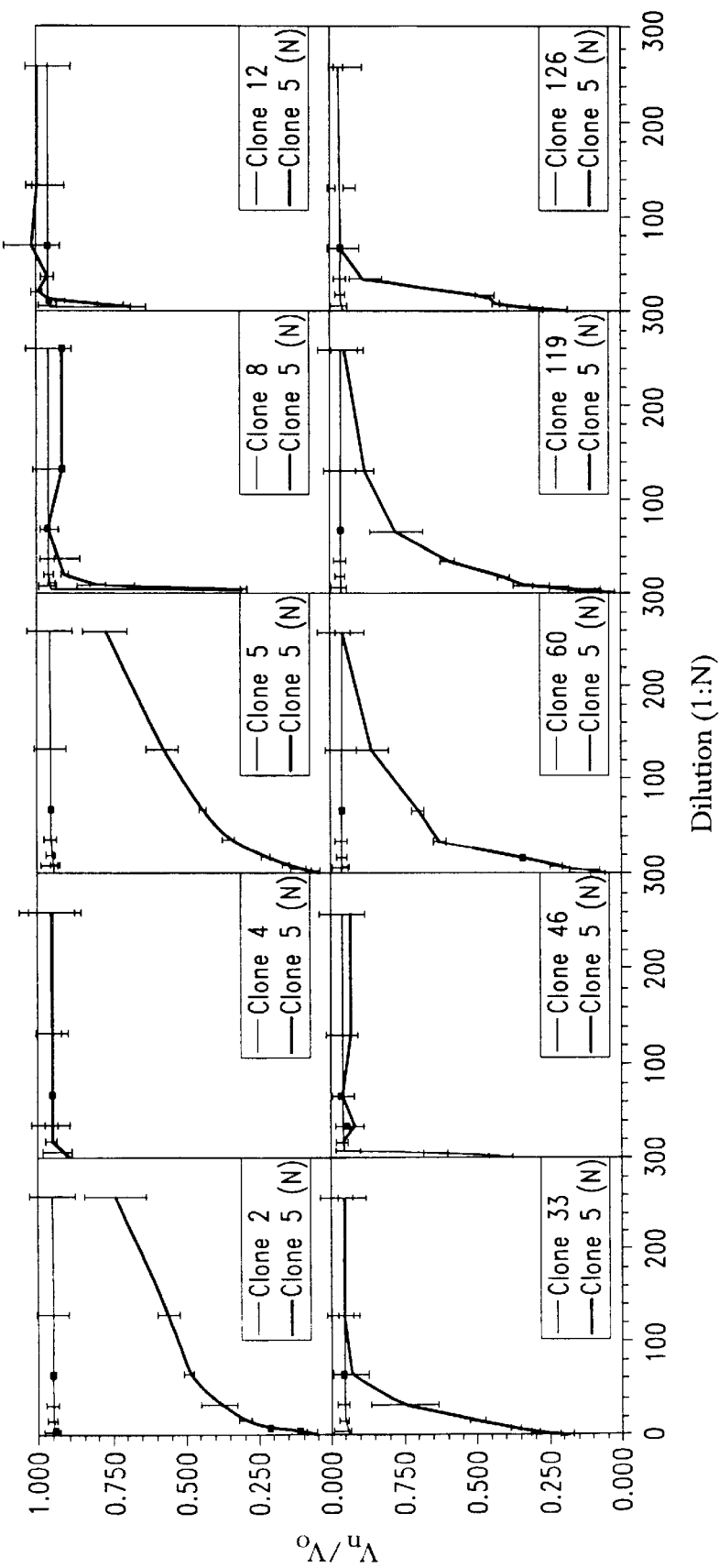

|        | FR1                        | CDR1         |
|--------|----------------------------|--------------|
| CL46   | LQEPGPGLVAPSQNLSISCTVSGS-  | SLSTLGIG-    |
| CL60   | LQEPGPGLVAPSQNLSISWTVSGS-  | SLSTLGIG-    |
| CL119  | VQEPGPGLVAPSQNLSISCTVSGS-  | SLSTLGIG-    |
| CL126  | LQEPGPGLVAPSQNLSISCTVSGS-  | SLSTLGIG-    |

|        | FR2                 | CDR2                  |
|--------|---------------------|-----------------------|
| CL46   | VRQPPGKGLEWLGVI-    | WAGGTTNYNLALMS-       |
| CL60   | VRQPPGKGLEWLGVI-    | WAGGTTNYNLALMS-       |
| CL119  | VRQPPGKGLEWLGVI-    | WAGGTTNYNLALMS-       |
| CL126  | VRQPPGKGLEWLGVI-    | WAGGTTNYNLALMS-       |

|        | FR3                                |
|--------|------------------------------------|
| CL46   | RLRISKDNSKSQVFLKMNSLQTDDTGMYFCAR-  |
| CL60   | RLRISKDNSKSQVFLKMNSLQNDDHSAHVLQR-  |
| CL119  | RLSISKDNSKSQVFLKMNSLTDDTAMYFCAR-   |
| CL126  | RLSISKDNSKSQVFLKMNRLQTDDTDMYFCAR-  |

|        | CDR3                | FR4              |
|--------|---------------------|------------------|
| CL46   | GLPRLLGAREHSHSLL-   | SQNDNPHRSDPWNS   |
| CL60   | ATETTGGAGKPLPTGL-   | PQGKKDNPHWVGIPRI |
| CL119  | GLPRLLGAREHSHSLL-   | RQNDNPIGRV       |
| CL126  | GLPENYWGAREHFPQA-   | SQAKRKTPIGSGF    |

FIG. 8

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CCAGGTTCTA GATGTATGGA CATCGTGATG ACBCAGWCTC C         41

( 2 ) INFORMATION FOR SEQ ID NO:2:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

ACTGTGGCTG CACCAGAAGG TAAATCTTCC GGTTCTGGCT CCGAATCTAA ATCTTATCAG         60

( 2 ) INFORMATION FOR SEQ ID NO:3:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GGCTCCGAAT CTAAATCTTA TCAGGTGCAG CTGGTGSAGT SKGG         44

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:4:

TCCACCAAGG GCCCATAGGT CTGAATTCTG 30

( 2 ) INFORMATION FOR SEQ ID NO:5:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:5:

Leu Gln Glu Pro Gly Pro Gly Leu Val Ala Pro Ser Gln Asn Leu Ser
1               5                   10                  15

Ile Ser Cys Thr Val Ser Gly Ser Ser Leu Ser Thr Leu Gly Ile Gly
                20                  25                  30

( 2 ) INFORMATION FOR SEQ ID NO:6:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:6:

Leu Gln Glu Pro Gly Pro Gly Leu Val Ala Pro Ser Gln Asn Leu Ser
1               5                   10                  15

Ile Ser Trp Thr Val Ser Gly Ser Ser Leu Ser Thr Leu Gly Ile Gly
                20                  25                  30

( 2 ) INFORMATION FOR SEQ ID NO:7:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:7:

Val Gln Glu Pro Gly Pro Gly Leu Val Ala Pro Ser Gln Asn Leu Ser
1               5                   10                  15

Ile Ser Cys Thr Val Ser Gly Ser Ser Leu Ser Thr Leu Gly Ile Gly
                20                  25                  30

( 2 ) INFORMATION FOR SEQ ID NO:8:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:8:

Leu Gln Glu Pro Gly Pro Gly Leu Val Ala Pro Ser Gln Asn Leu Ser
1               5                   10                  15

```
          Ile  Ser  Cys  Thr  Val  Ser  Gly  Ser  Ser  Leu  Ser  Thr  Leu  Gly  Ile  Gly
                         20                      25                           30
```

( 2 ) INFORMATION FOR SEQ ID NO:9:

( i ) SEQUENCE CHARACTERISTICS:
        ( A ) LENGTH: 29 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:9:

```
          Val  Arg  Gln  Pro  Pro  Gly  Lys  Gly  Leu  Glu  Trp  Leu  Gly  Val  Ile  Trp
          1                   5                        10                         15

Ala  Gly  Gly  Thr  Thr  Asn  Tyr  Asn  Leu  Ala  Leu  Met  Ser
                         20                      25
```

( 2 ) INFORMATION FOR SEQ ID NO:10:

( i ) SEQUENCE CHARACTERISTICS:
        ( A ) LENGTH: 29 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:10:

```
          Val  Arg  Gln  Pro  Pro  Gly  Lys  Gly  Leu  Glu  Trp  Leu  Gly  Val  Ile  Trp
          1                   5                        10                         15

Ala  Gly  Gly  Thr  Thr  Asn  Tyr  Asn  Leu  Ala  Leu  Met  Ser
                         20                      25
```

( 2 ) INFORMATION FOR SEQ ID NO:11:

( i ) SEQUENCE CHARACTERISTICS:
        ( A ) LENGTH: 29 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:11:

```
          Val  Arg  Gln  Pro  Pro  Gly  Lys  Gly  Leu  Glu  Trp  Leu  Gly  Val  Ile  Trp
          1                   5                        10                         15

Ala  Gly  Gly  Thr  Thr  Asn  Tyr  Asn  Leu  Ala  Leu  Met  Ser
                         20                      25
```

( 2 ) INFORMATION FOR SEQ ID NO:12:

( i ) SEQUENCE CHARACTERISTICS:
        ( A ) LENGTH: 29 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:12:

```
          Val  Arg  Gln  Pro  Pro  Gly  Lys  Gly  Leu  Glu  Trp  Leu  Gly  Val  Ile  Trp
          1                   5                        10                         15

Ala  Gly  Gly  Thr  Thr  Asn  Tyr  Asn  Leu  Ala  Leu  Met  Ser
                         20                      25
```

( 2 ) INFORMATION FOR SEQ ID NO:13:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:13:

```
Arg  Leu  Arg  Ile  Ser  Lys  Asp  Asn  Ser  Lys  Ser  Gln  Val  Phe  Leu  Lys
1                   5                        10                       15
Met  Asn  Ser  Leu  Gln  Thr  Asp  Asp  Thr  Gly  Met  Tyr  Phe  Cys  Ala  Arg
               20                      25                       30
```

( 2 ) INFORMATION FOR SEQ ID NO:14:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:14:

```
Arg  Leu  Arg  Ile  Ser  Lys  Asp  Asn  Ser  Lys  Ser  Gln  Val  Phe  Leu  Lys
1                   5                        10                       15
Met  Asn  Ser  Leu  Gln  Asn  Asp  Asp  His  Ser  Ala  His  Val  Leu  Gln  Arg
               20                      25                       30
```

( 2 ) INFORMATION FOR SEQ ID NO:15:

( i ) SEQUENCE CHARACTERISTICS:
        ( A ) LENGTH: 31 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:15:

```
Arg  Leu  Ser  Ile  Ser  Lys  Asp  Asn  Ser  Lys  Ser  Gln  Val  Phe  Leu  Lys
1                   5                        10                       15
Met  Asn  Ser  Leu  Thr  Asp  Asp  Thr  Ala  Met  Tyr  Phe  Cys  Ala  Arg
               20                      25                       30
```

( 2 ) INFORMATION FOR SEQ ID NO:16:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:16:

```
Arg  Leu  Ser  Ile  Ser  Lys  Asp  Asn  Ser  Lys  Ser  Gln  Val  Phe  Leu  Lys
1                   5                        10                       15
Met  Asn  Arg  Leu  Gln  Thr  Asp  Asp  Thr  Asp  Met  Tyr  Phe  Cys  Ala  Arg
               20                      25                       30
```

( 2 ) INFORMATION FOR SEQ ID NO:17:

( i ) SEQUENCE CHARACTERISTICS:

(A) LENGTH: 30 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:17:

Gly Leu Pro Arg Leu Leu Gly Ala Arg Glu His Ser His Ser Leu Leu
1               5                   10                  15

Ser Gln Asn Asp Asn Pro His Arg Ser Asp Pro Trp Asn Ser
            20                  25                  30

(2) INFORMATION FOR SEQ ID NO:18:

(i) SEQUENCE CHARACTERISTICS:
(A) LENGTH: 32 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:18:

Ala Thr Glu Thr Thr Gly Gly Ala Gly Lys Pro Leu Pro Thr Gly Leu
1               5                   10                  15

Pro Gln Gly Lys Lys Asp Asn Pro His Trp Val Gly Ile Pro Arg Ile
            20                  25                  30

(2) INFORMATION FOR SEQ ID NO:19:

(i) SEQUENCE CHARACTERISTICS:
(A) LENGTH: 26 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:19:

Gly Leu Pro Arg Leu Leu Gly Ala Arg Glu His Ser His Ser Leu Leu
1               5                   10                  15

Arg Gln Asn Asp Asn Pro Ile Gly Arg Val
            20                  25

(2) INFORMATION FOR SEQ ID NO:20:

(i) SEQUENCE CHARACTERISTICS:
(A) LENGTH: 29 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:20:

Gly Leu Pro Glu Asn Tyr Trp Gly Ala Arg Glu His Phe Pro Gln Ala
1               5                   10                  15

Ser Gln Ala Lys Arg Lys Thr Pro Ile Gly Ser Gly Phe
            20                  25

(2) INFORMATION FOR SEQ ID NO:21:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:21:

TTATTACTCG CTGCCCAACC AGCG 24

(2) INFORMATION FOR SEQ ID NO:22:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:22:

CTGATAAGAT TTAGATTC 18

(2) INFORMATION FOR SEQ ID NO:23:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:23:

GGCTCCGAAT CTAAATCTTA TCAG 24

(2) INFORMATION FOR SEQ ID NO:24:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:24:

AAAGGCCGCT TTTGCGGGAT CGTC 24

METHODS AND COMPOSITIONS COMPRISING SINGLE CHAIN RECOMBINANT ANTIBODIES

FIELD OF THE INVENTION

The field of the invention is recombinant single chain antibodies.

BACKGROUND OF THE INVENTION

Generation of recombinant human antibodies is a useful means of providing a diverse array of antibodies directed against a variety of infectious agents. Methods for the generation of such antibodies include the use of bacterial expression vectors and combinatorial approaches using phage surface display libraries. Neutralizing antigen-binding fragments from a combinatorial phage surface display library have been developed wherein heavy and light chains are first individually cloned and are then subsequently combined to generate single chain antigen-binding fragments (Barbas et al., 1992, Proc. Natl. Acad. Sci. USA 89:9339–9343).

Single chain antibodies are useful for the diminution or ablation of disease states in humans for which there is limited treatment at present, for example, infection of humans with HIV. In particular, mother to child transmission of HIV-1 may be preventable by treating an HIV-infected mother with single chain antibodies. Transmission of HIV from mother to child is variable with transmission rates of 20–60% being reported (Blanche et al., 1989, New Eng. J. Med. 320:1643–1648). Three possible windows for viral spread from mother to child are the intrauterine, intrapartum, and postpartum periods (MacDonald, 1991, J. Acquired Immun. Defic. Syndr. 4:100–108). Low maternal CD4+ cell levels, viremia, p24 antigenemia and impaired T-cell function all correlate with increased rates of transmission (Lindgren et al., 1991, AIDS 5:111–116; Newell et al., 1992, Lancet 339:1007–1012; Scartti et al., 1993, Proc. Natl. Acad. Sci. USA 90:1721–1725). Maternal-fetal transmission has also been reported to correlate with the absence of antibodies to the V3 loop of gp120 in the mothers (Goedert et al., 1989, Lancet ii:1351–1354). Studies by Fiore et al. (1993, AIDS 7:29–31) suggest that high seroreactivity is more prevalent in sera obtained from nontransmitting mothers. Specific antibody responses to limited epitopes of gp120 have similarly been correlated with a reduced rate of vertical transmission (Rossi et al., 1989, Proc. Natl. Acad. Sci. USA 86:8055–8058). A high diversity of antibody reactivity to epitopes within gp160, including epitopes in gp120 as well as gp41, and increased neutralizing titer have also been reported to be associated with maternal nontransmitter status (Ugen et al., 1992, J. Clin. Invest. 89:1923–1930).

Immunoglobulin (Ig) therapy has been used with some efficacy in both HIV-1-infected adults and children (Calvelli et al., 1986, Pediatric. Infect. Dis. J. 5: Supp. S207–S210; Ugen et al., 1994, AIDS Reader 4:66–71) and in chimpanzees (Prince et al., 1991, AIDS Res. Human Retroviruses 7:971–973). Therefore, development and use of a large pool of human monoclonal antibodies (MAb) or replacement antibodies remains a goal for passive immunization strategies (Osther et al., 1991, Hybridoma 10:673–683; Putney et al., 1992, Trends Biochem Sci. 17:191–196). Recombinant human MAb have been developed through Epstein-Barr virus transformation of primary B cells. However, these transformed cells are unstable and often present additional technical difficulties. Different expression vectors have been used to produce MAb including yeast (Horowitz et al., 1988, Proc. Natl. Acad. Sci. USA 85:8678–8682), *E. coli* (Skerra et al., 1988, Science 240:1037–1041; Better et al., 1988, Science 240:1041–1043), and baculovirus (Hasemann et al., 1990, Proc. Natl. Acad. Sci. USA 87:3942–3946) vectors. However, use of the aforementioned technology involves labor intensive and often problematic screening.

Recombinant MAb have also been generated using combinatorial libraries expressed in bacteriophage lambda vectors (Huse et al., 1989, Science 246:1275–1281). Further, modified filamentous phage combinatorial antibody libraries have been developed that allow rapid affinity-based screening of millions of clones (Smith, 1985, Science 228:1315–1316; Kang et al., 1991, Proc. Natl. Acad. Sci. USA 88:4363–4366; Barbas et al., 1991, Proc. Natl. Sci. USA 88: 7978–7982). Using this approach, recombinant human MAb have been generated against: HIV-1, respiratory syncytial virus, hepatitis B surface antigens, herpes simplex virus types 1 and 2, human cytomegalovirus, varicella zoster virus, and rubella virus (Burton et al., 1991, Proc. Natl. Acad. Sci. USA 88:10134–10137; Barbas et al., 1992, Proc. Natl. Acad. Sci. USA 89:9339–9343; Barbas et al., 1992, Proc. Natl. Acad. Sci. USA 89:10164–10168; Zebedee et al., 1992, Proc. Natl. Acad. Sci. USA 89:3175–3179; Williamson et al., 1993, Proc. Natl. Acad. Sci. USA 90:4141–4145).

There is a need in the art for an efficient and rapid means of producing antibodies comprising human sequences which specifically bind viral antigens. Such antibodies would permit passive immunotherapy without provoking an immune response against the therapeutic agent. Passive immunotherapy against viruses using recombinant human antibodies would therefore provide a new therapeutic tool against diseases for which there are few therapeutic solutions at present.

SUMMARY OF THE INVENTION

The invention features a method of generating a recombinant single chain antibody molecule, the method comprises amplifying a nucleic acid sequence encoding a heavy chain and a nucleic acid sequence encoding a light chain of an antibody molecule to generate a heavy and a light chain specific DNA sequence; amplifying by PCR SOE the heavy and light chain specific DNA using a light chain specific 3' primer and a heavy chain specific 5' primer wherein at least 5 contiguous nucleotides of each of the 3' and 5' primers are complementary to each other and then expressing the recombinant single chain antibody so amplified.

By "recombinant single chain antibody molecule" as used herein is meant a peptide having a heavy and a light antibody chain component with a flexible linker positioned therebetween, which peptide is encoded by a DNA generated by recombinant DNA technology.

By "PCR-SOE" as used herein is meant a method of performing PCR using a 3' primer specific for a first DNA sequence and a 5' primer specific for a second DNA sequence wherein each primer contains linker sequences, a portion of each of which linker sequences are complementary to each other., The invention also features a method of generating an isolated DNA sequence encoding a recombinant single chain antibody molecule, the method comprises amplifying a nucleic acid sequence encoding a heavy chain and a nucleic acid sequence encoding a light chain of an antibody molecule to generate a heavy and a light chain specific DNA sequence; amplifying by PCR SOE the heavy and light chain specific DNA using a light chain specific 3' primer and a heavy chain specific 5' primer wherein at least 5 contiguous nucleotides in each of the 3' and 5' primers are complementary to each other, and isolating DNA sequence so amplified.

Also featured in the invention is an isolated DNA encoding the single chain antibody molecule of the invention.

By "isolated DNA" as used herein is meant a DNA sequence which has been purified from the sequences which flank it in a naturally occurring state, e.g., a DNA sequence which has been removed from the sequences which are normally adjacent to the DNA sequence, i.e., those sequences which are adjacent to the DNA sequence in the genome in which it naturally occurs. The term also applies to a DNA sequence which has been substantially purified from other components which naturally accompany it, such as RNA, protein and lipid, i.e., those components which naturally accompany it in a cell. Isolated DNA sequence also denotes a synthetically prepared DNA sequence corresponding to the cloned sequence.

In one aspect, the recombinant single chain antibody molecule is directed against a Human Immunodeficiency virus antigen. In another aspect, the recombinant single chain antibody molecule is directed against Human Immunodeficiency virus type 1 gp120. In yet another aspect, the recombinant single antibody chain molecule is selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19 and SEQ ID NO:20.

Also featured in the invention is an isolated DNA encoding a recombinant single chain antibody molecule directed against Human Immunodeficiency Virus gp120.

The invention also includes a method of treating a human infected with Human Immunodeficiency Virus comprising administering to the human a pharmaceutical composition comprising a recombinant single chain antibody molecule generated by a method comprising amplifying a nucleic acid sequence encoding a heavy chain and a nucleic acid sequence encoding a light chain of an antibody molecule to generate a heavy and a light chain specific DNA sequence; amplifying by PCR SOE the heavy and light chain specific DNA using a light chain specific 3' primer and a heavy chain specific 5' primer wherein at least 5 contiguous nucleotides of each of the 3' and 5' primers are complementary to each other and then expressing the recombinant single chain antibody so amplified.

The invention further features a method of treating a human infected with Human Immunodeficiency Virus comprising administering to the human a pharmaceutical composition comprising a recombinant single chain antibody molecule selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19 and SEQ ID NO:20.

The invention further includes a kit comprising a recombinant single chain antibody molecule generated by a method comprising amplifying a nucleic acid sequence encoding a heavy chain and a nucleic acid sequence encoding a light chain of an antibody molecule to generate a heavy and a light chain specific DNA sequence; amplifying by PCR SOE the heavy and light chain specific DNA using a light chain specific 3' primer and a heavy chain specific 5' primer wherein at least: 5 contiguous nucleotides of each of the 3' and 5' primers are complementary to each other and then expressing the recombinant: single chain antibody so amplified. The kit may comprise a recombinant single chain antibody molecule selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19 and SEQ ID NO:20.

The invention also includes a vector named pMARS8. The vector of the invention facilitates cloning of the variable regions of kappa light and heavy chains together as a single chain antibody molecule.

THE DRAWINGS

FIG. 1 is a diagram depicting construction of the plasmid pMARS8. RBS, ribosome binding site; pBS KS+, plasmid Bluescript vector KS+.

FIG. 2 is a diagram including the sequence of the oligonucleotide primers used for amplification of heavy and kappa chains and for splicing by overlap extension methods. The relative positions and the sequence of the oligonucleotide primers are shown. FR1, Framework 1; CDR, complementarity determining region. $5'$-$V_L$ [SEQ ID NO:1], $3'$-$V_L$ (LINK) [SEQ ID NO:2], $5'$-(LINK)-$V_H$ [SEQ ID NO:3] and $3'$-$V_H$ [SEQ ID NO:4].

FIG. 3 is a photograph of a gel depicting PCR amplification of heavy chain and kappa and lambda light chain Fv regions. RNA from human peripheral blood monocytes obtained from an asymptomatic HIV-1-positive mother was used to amplify heavy and light chains separately giving rise to products of approximately 400 base pairs. The heavy chain is slightly bigger than the light chain. An 800 base pair product was obtained by splicing by overlap extension (SOE) PCR of heavy plus kappa sequences and heavy plus lambda sequences.

FIG. 4 is a photograph depicting Western blot analysis of expression of soluble Fv proteins. Representative clones comprising immunoglobulin inserts as well as clones which comprise only the vector sequences were analyzed. Expression in bacteria comprising these clones was induced with isopropyl thiogalactose. Bacterial lysates obtained by sonication were electrophoresed through sodium dodecyl sulfate polyacrylamide gels and analyzed by Western blotting using anti-human antigen-binding fragments conjugated to horse radish peroxidase. A 37 kD band representing Fv protein is present in lanes containing material obtained from clones comprising immunoglobulin inserts which band is absent in lanes containing material obtained from clones comprising only vector sequences.

FIG. 5 is a graph depicting enzyme linked immunosorbant assay (ELISA) analysis of soluble Fv fragments directed against HIV-1 gp120. Clones 2, 4, 5, 8, 12, 22, 33, 46, 119 and 126 are all positive clones. The values shown are subtracted from background values. OD, optical density.

FIG. 6 is a diagram depicting gross epitope mapping of recombinant Fv clones using vaccinia virus lysates. The different binding patterns of each of the clones in an ELISA is shown. aa, amino acid.

FIGS. 7A–7J are series of graphs depicting neutralization assays of recombinant Fv clones using MT-2 cells and HIV-$I_{IIIB}$. The virus surviving fraction is $V_n/V_0$ versus the dilution of Fv obtained from different clones. Clone 5(N) is a negative clone containing an immunoglobulin insert which does not bind to gp120. The mean±SD of triplicate wells is shown.

FIG. 8 comprises the sequence analysis of Fv clones showing the $V_H$ region. CL, clone; FR1, framework I; FR2, framework II; FRF3, framework III; FR4, framework IV; CDR, complementarity determining region. The SEQ ID NOS of the listed sequences are as follows: CL46/FR1/CDR1 [SEQ ID NO:5]; CL60/FR1/CDR1 [SEQ ID NO:6]; CL119/FR1/CDR1 [SEQ ID NO:7]; CL126/FR1/CDR1 [SEQ ID NO:8]; CL46/FR2/CDR2 [SEQ ID NO:9]; CL60/FR2/CDR2 [SEQ ID NO:10]; CL119/FR2/CDR2 [SEQ ID NO:11]; CL126/FR2/CDR2 [SEQ ID NO:12]; CL46/FR3 [SEQ ID NO:13]; CL60/FR3 [SEQ ID NO:14]; CL119/FR3 [SEQ ID NO:15]; CL126/FR3 [SEQ ID NO:16]; CL46/CDR3/FR4 [SEQ ID NO:17]; CL60/CDR3/FR4 [SEQ ID NO:18]; CL119/CDR3/FR4 [SEQ ID NO:19]; and, CL126/CDR3/FR4 [SEQ ID NO:20].

DETAILED DESCRIPTION

Figure 1:
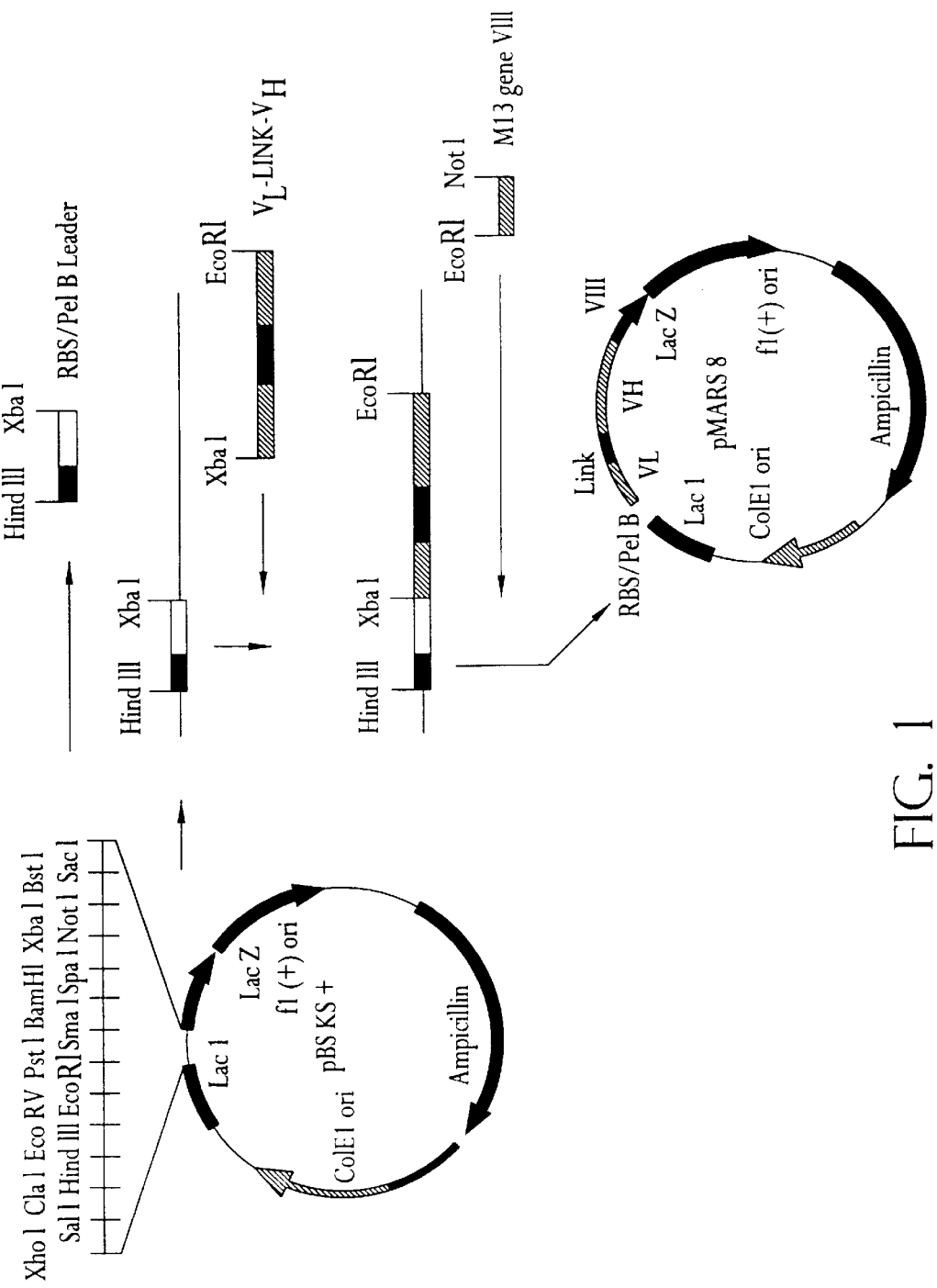

According to the methods of the invention, a simple vector system has been developed which facilitates cloning of the variable regions of kappa light and heavy chains together as a single chain Fv molecule. This method of the invention circumvents the need for producing a combinatorial vector. Instead, a vector, pMARS8, has been developed by modification of the Bluescript vector (Stratagene, La Jolla, Calif.). Kappa, heavy, and lambda immunoglobulin chains are amplified separately and are subsequently combined as single chains, using recombinant PCR, i.e., the splicing by overlap extension (SOE) PCR method, wherein the single chains comprise a heavy chain plus a kappa chain or a heavy chain plus a lambda chain. Flexible linear-linker peptides are used in the primers which therefore comprise the linker used to join $V_L$ to $V_H$ to form the novel recombinant Fv fragments of the invention containing variable regions comprising both light and heavy chains as a single chain. The Fv fragments of the invention may be developed as a library directed against any pathogen, including HIV-1, and in particular against the HIV gp120 antigen.

The invention also features a simple vector for cloning human antibody-derived binding proteins, named pMARS8, which is generated as described herein in Example 1.

Also featured in the invention is a panel of isolated human Fv fragments derived from an asymptomatic seropositive HIV-infected nontransmitter mother, which fragments bind to HIV-1 gp120. These recombinant human antibodies are important in that they may form the basis for methods of treatment, prevention and diagnosis of HIV infection.

As noted above, novel recombinant Fv fragments containing variable regions of light and heavy chains as a single chain may be developed as a library of antibodies directed against any pathogen according to the methods of the invention. Such pathogens include, but are not limited to, viruses, bacteria and fungi. Additional viral pathogens against which the method and antibodies of the invention are useful include, but are not limited to, rotavirus, rabies virus, hepatitis virus types A, B, C, D, and E and herpesviruses, including herpes simplex viruses type 1 and 2, varicella zoster virus, cytomegalovirus, Epstein Barr virus and human herpesviruses 6 and 7.

Further, the method of the invention is not limited to the generation of sFvs directed against the antigens of pathogens. The method may also be used to generate antibodies directed against cellular antigens of a mammal which when bound to the appropriate sFv confers a beneficial effect upon the mammal. Examples of such antigens include, but are not limited to, tumor-associated antigens, autoimmune disease-associated antigens, and antigens associated with neurodegenerative disorders and muscular disorders. The types of cancer which may be treated using the methods and antibodies of the invention include, but are not limited to, breast and colon cancer and lymphoma. Anti-idiotype antibodies which may be produced using the method of the invention may be useful for treatment of myasthenia gravis, systemic lupus erythematosus, Grave's disease, diabetes and other T cell autoimmune diseases.

Those of skill in the art of a particular disease and having an understanding of the nature of the target antigen will know how to make a single chain Fv antibody directed against that antigen following the procedures described herein. The preferred disease against which antibodies of the invention are directed is HIV-1 infection and/or AIDS. The preferred target antigen is HIV-1 gp120.

Generation of the Fv fragments of the invention is accomplished as follows. The well known Bluescript KS+ vector (Stratagene, La Jolla, Calif.) is modified in order to render it: suitable for expression of the Fv fragments of the invention. Gene VIII of M13 phage is incorporated into this vector such that the Fv fragments cloned therein are expressed on the surface of the phage. Next, the variable regions of heavy and light chains are combined by PCR-SOE which facilitates generation of a single chain library in a single step. This procedure also serves to simplify screening of clones so generated. The method is simple and effective for the expression of Fv antibody genes in vitro.

Figure 2:
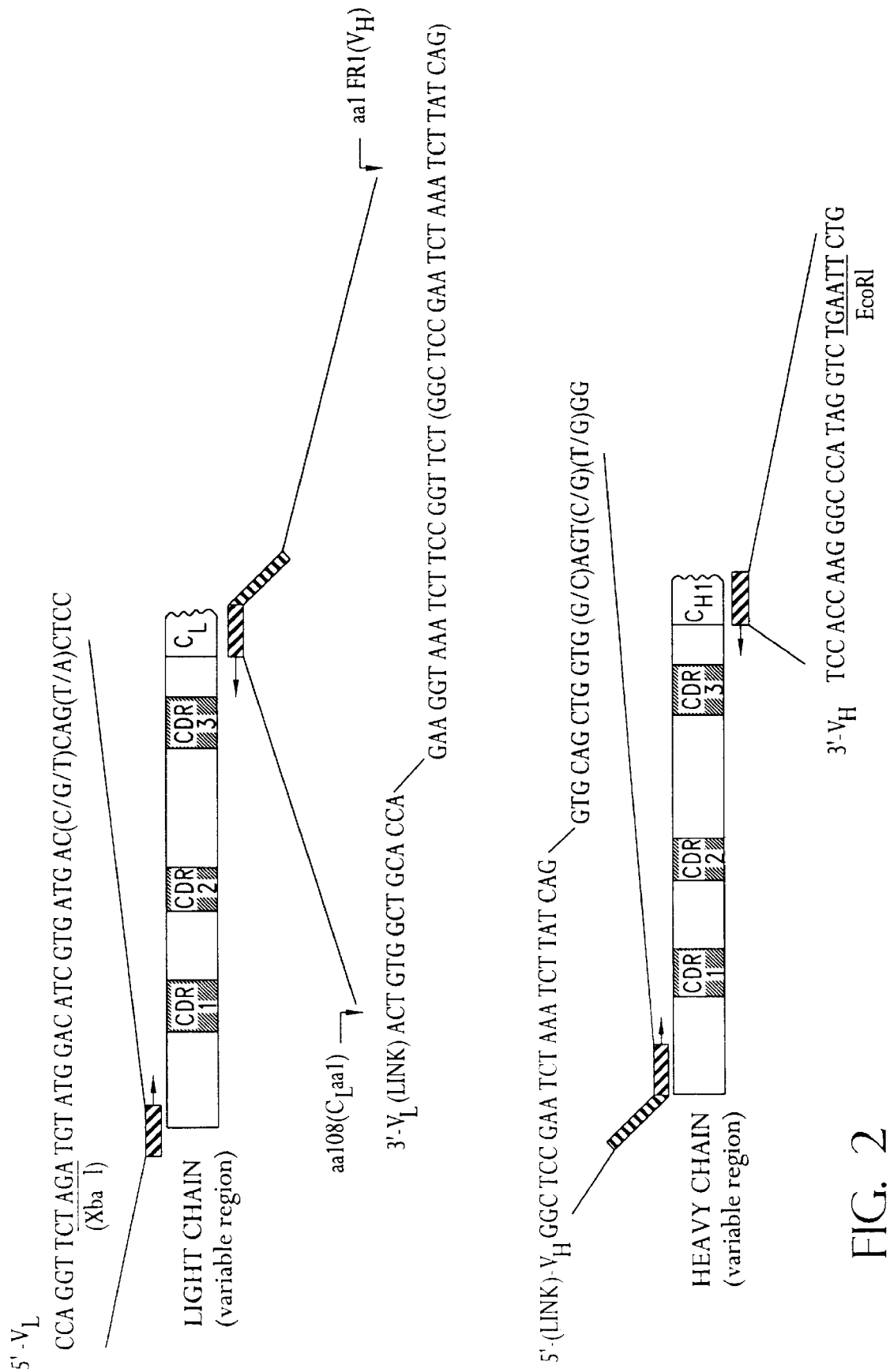

To generate sFvs directed against a particular antigen, cells are isolated from a patient, which cells express RNA encoding an antibody directed against that antigen. A cDNA copy of the RNA is generated which is then amplified by PCR using primers specific for IgG. $V_H$ and $V_L$ DNA specific: fragments are separately isolated and purified. A second round of PCR is then performed wherein the 3' primer specific for the light chain and the 5' primer specific for the heavy chain contains linker sequences, a portion of each of which are complementary to each other. Examples of such linkers are shown in FIG. 2. Any linkers having this or another complementary sequence fused to light or heavy chains are also useful in the invention. For example, linkers such as those disclosed in Brinkmann et al. (1993, Proc. Natl. Acad. Sci. USA 90:7538), Davis et al. (1991, Biotechnology 9:165) or Sarantopoulos et al. (1994, J. Immunol. 152:5344) may also be used to generate the sFv's of the invention.

The above-mentioned round of PCR is conducted under conditions, using the aforementioned primers, which results in PCR fragments which are generated by the SOE method. The SOE method is exemplified herein in Example 3. The complementary portion of each of the 5' and 3' linker sequences is from at least five to at least thirty three or more contiguous nucleotides, and any an all increments therebetween. Preferably, the complementary portion of each of the 5' and 3' linker sequences is from at least nine to at least thirty three contiguous nucleotides.

The PCR products so generated are purified and are ligated into a suitable expression vector, for example, any number of vectors described in Sambrook et al. (1989, Molecular Cloning: A Laboratory Manual, Cold Spring Harbor, N.Y.). Cells are transformed with the recombinant sequences to generate a library which is then screened for expression of the appropriate sFv by panning or any other similar screening technique. Expressed sFv is further examined for the desired activity by Western blotting, ELISA and other techniques well known in the art.

The invention provides an isolated DNA encoding a single chain antibody generated by the method of the invention. The isolated DNA of the invention should be construed to include DNAs which are substantially homologous to DNA encoding the single chain antibody of the invention. Preferably, the isolated DNA of the invention includes DNA which is substantially homologous to any of the DNAs encoding the peptides of SEQ ID NOS:5–20, provided that such DNAs encode single chain antibodies having the properties described herein. Further, the invention should be construed to include single chain antibody molecules comprising amino acid sequences which share substantial homology with the peptides of SEQ ID NOS:5–20, having the properties described herein.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

By "substantial homology" as used herein referring to a nucleic acid sequence, is a nucleic acid sequence which is at least 50% homologous, preferably 60% homologous, more preferably 80k homologous and most preferably 90k homologous to DNA encoding the peptides of SEQ ID NOS:5–20 disclosed herein. By "substantial homology" as used herein referring to an amino acid sequence, is an amino acid sequence which is at: least 50% homologous, preferably 60% homologous, more preferably 80% homologous and most preferably 90% homologous to the peptides of SEQ ID NOS:5–20 disclosed herein.

The starting point for the method of the invention is a human who has produced antibodies to the target antigen. While this method is applicable to known virus strains, it is not necessary that the serology of the virus strain be fully characterized. The invention also therefore contemplates use of the method to produce sFvs directed against virus strains which have not been previously characterized. In the midst of an epidemic, for example, the method of the invention provides antibodies which are specific for the particular virus strain causing the outbreak, without the need for extensive laboratory study of the virus strain. Once the immune system has been exposed to antigen and the patient's B cells have been stimulated, rearranged immunoglobulin genes encoding variable regions specific for antigenic determinants on the specific virus strain causing the disease will be present in the peripheral blood lymphocyte population. RNA extracted from these cells may therefore be used to generate sFvs directed against viral antigens which sFvs may be useful as immunotherapeutic agents against the disease.

The compositions and methods of the invention have several advantages over traditional antibodies and methods for their generation. Fv fragments are smaller than their traditional counterparts and may therefore expose antigen-binding sites potentially more efficiently. Further, higher levels of expression of single chain Fv may be achieved using the methods of the invention than can be achieved using the traditional combinatorial screening method.

Further, the recombinant antibody molecules possess traditional antibody-based biological activities which may be extremely valuable as diagnostic and therapeutic reagents and may therefore serve as the basis for development for example, of a battery of reagents capable of treating HIV-infected individuals. In fact, the specific Fv fragments disclosed herein, since they are derived from a non-transmitter HIV-1 infected mother, may be useful either directly as therapeutic agents to treat HIV infection in both males and females, or they may be useful indirectly in that they may serve as a basis from which other useful therapeutics may be developed.

The antibodies of the invention may also be used as therapeutic agents for treatment of a disease state associated with the production of an antigen, which disease state is diminished or ablated when the subject antigen is bound to an appropriate antibody. Binding of antibody to antigen may occur in any cell, tissue or bodily fluid wherein antigen is expressed and into which the antibody is delivered. The antibody is delivered to the cell, tissue or bodily fluid of the patient using traditional routes of administration of such proteins in humans. Such proteins are administered to a human in one of the traditional modes (e.g., orally, parenterally, transdermally or transmucosally), in a sustained release formulation using a biodegradable biopolymer, or by on-site delivery using micelles, gels and liposomes, or rectally (e.g., by suppository or enema). The antibodies may be administered to the human in a dosage of 0.1 µg/kg/day to 50 mg/kg/day, either daily or at intervals sufficient to ablate or diminish the disease state. Precise formulations and dosages may be determined using standard techniques, by a pharmacologist of ordinary skill in the art.

The present invention further provides pharmaceutical compositions useful in providing passive immunity against HIV. Such compositions are useful for administration to individuals anticipating risk of exposure to the HIV virus, e.g., prior to surgery or for health-care workers.

These compositions comprise one or more antibodies of the invention and a suitable carrier or diluent. Carriers may be selected by one of skill in the art. Exemplary carriers include sterile saline, lactose, sucrose, calcium phosphate, gelatin, dextrin, agar, pectin, peanut oil, olive oil, sesame oil, and water. Additionally, the carrier o:r diluent may include a time delay material, such as glycerol monostearate or glycerol distearate alone or with a wax. In addition, slow release polymer formulations can be used. Additionally, this composition may further contain other active ingredients including, for example, AZT, DDC, DDI, biological response modifiers, such as interleukins, colony stimulating factors, especially GM-CSF, INFs, and other immunostimulatory cytokines, as well as preservatives, or chemical stabilizers.

Suitable dosages can be determined by the attending physician, with reference to the discussion herein relating to appropriate doses for the therapeutic and vaccinal. compositions of the invention. The composition administration may be by any appropriate route and repeated as necessary as described herein.

An alternative, desirable vaccine composition may contain a conventional bio-expression vector, such as an adenovirus, poliovirus, vaccinia virus or retrovirus, into which the sequences of one or more of the HIV antibodies, or functional fragments thereof are inserted under the control of the viral expression regulatory sequences [see, e.g., U.S. Pat. No. 4,920,209 which is hereby incorporated herein by reference]. Such viral vector compositions can be employed to deliver the relevant peptide or antibody sequences to the patient.

Optionally, the vaccine composition may further contain adjuvants, preservatives, chemical stabilizers, or other antigenic proteins. Typically, stabilizers, adjuvants, and preservatives are optimized to determine the best formulation for efficacy in the vaccinee. Suitable preservatives include chlorobutanol, potassium sorbate, sorbic acid, sulfur dioxide, propyl gallade, the parabens, ethyl vanillin, glycerin, phenol, parachlorophenol.

One or more of the above described vaccine components may be admixed or adsorbed with a conventional adjuvant. The adjuvant is used as a non-specific irritant to attract leukocytes or enhance an immune response. Such adjuvants include, among others, mineral oil and water, BCG, aluminum hydroxide, Avridine, L121/squalene, D-lactide-polylactide/glycoside, muramyl dipeptide, killed Bordetella, saponins, as Quil A.

Suitable amounts of the active ingredient can be determined by one of skill in the art based upon the level of immune response desired. In general, however, the vaccine composition contains between 1 ng to 1000 mg peptide and more preferably, 0.05 $\mu$g to 1 mg per ml, whether a single HIV peptide of the invention or a combination of these peptides or peptide constructs is employed. Antigens to other pathogens, such as measles, mumps, and rubella (MMR) vaccines, may be combined in a vaccine composition of the invention.

Suitable doses of the vaccine composition of the invention can be readily determined by one of skill in the art. Generally, a suitable dose is between 0.1 to 5 ml of the vaccine composition. Further, depending upon the patient being treated, i.e. weight, age, sex and general health, the dosage can also be determined readily by one of skill in the art.

The present invention also provides a prophylactic method entailing administering to a subject an effective amount of such a composition. For example, for prevention of vertical transmission, a vaccine composition of the invention could be administered either to a pregnant HIV-infected woman or an HIV-infected woman of child-bearing age. In general, the vaccine will be administered once, or preferably, more frequently depending on the likelihood of exposure to the virus. Where desirable, boosters may be administered. The vaccine may be administered by any suitable route. However, parenteral administration, particularly intramuscular, and subcutaneous, is the preferred route. Also preferred is the oral route of administration.

The antibodies identified herein as correlating with maternal non-transmission status can be used in active immunotherapy of HIV-positive individuals to initiate or boost their immune response of neutralizing antibodies.

Thus, the antibodies of this invention are useful as therapeutic compositions for treating subjects who test positive for, or, prior to testing, exhibit symptoms of, AIDS or a related non-symptomatic condition. In one therapeutic embodiment, one or more antibodies of the invention, preferably directed to more than one of the non-transmission associated or the transmission associated peptides, may be used therapeutically as targeting agents to deliver virus-toxic or infected cell-toxic agents to HIV infected cells. Rather than being associated with labels for diagnostic uses, a therapeutic agent employs the antibody linked to an agent or ligand capable of disabling the replicating mechanism of the virus or of destroying the virus infected cell. The identity of the toxic ligand does not limit the present invention. It is expected that preferred antibodies to the HIV peptides may be screened for the ability to internalize into the infected cell and deliver the ligand into the cell.

Such a therapeutic composition may be formulated to contain a carrier or diluent and one or more of the antibodies of the invention. Such carriers are discussed above in connection with vaccinal compositions.

Alternatively, or in addition to the antibodies of the invention, antagonists to HIV peptides are expected to be useful in reducing and eliminating disease symptoms. It should be noted that the antibodies of this invention may be used for the design and synthesis of either peptide or non-peptide compounds (mimetics) which would be useful in the same therapy as the antibodies [see, e.g., Saragovi et al., Science, 253:792–795 (1991)]. The development of therapeutic compositions containing these agents is within the skill of one of skill in the art in view of the teaching of this invention.

Optionally, this composition may also contain other therapeutic agents useful in treating HIV infection, such as those discussed above in connection with compositions for passive immunization. Suitable non-therapeutic ingredients which may be used in a therapeutic composition in conjunction with the antibodies of the invention include for example, casamino acids, sucrose, gelatin, and phenol red.

According to the method of the invention, a person may be treated for HIV infection by administering an effective amount of such a therapeutic composition. Preferably, such a composition is administered parenterally, preferably intramuscularly or subcutaneously. However, it may also be formulated to be administered by any other suitable route, including orally or topically.

A therapeutic composition of the invention may contain between about 0.05 $\mu$g/ml to about 1000 $\mu$g/ml of an antibody of the invention. Such a composition may be administered 1–3 times per day. However, suitable dosage adjustments may be made by the attending physician depending upon the age, sex, weight and general health of the patient.

The single chain antibody of the invention may be provided as a kit wherein the antibody is provided in a pharmaceutical carrier and the kit is accompanied by instructions for using the same.

The following provides some examples of the present invention. These examples are not to be considered as limiting the scope of the appended claims in any manner.

EXAMPLES

Example 1

Vector construction

The lac Z promoter, ribosome binding site and pectin lyase signal peptide (pel B) leader sequences were excised from the expression vector PDAB (McCallus et al., 1992, Viral Immunol. 5:163–172) at the HindIII and XbaI sites and were subcloned into the Bluescript KS+ vector (Stratagene cloning system, La Jolla, Calif., USA). Bacteriophage M13 gene VIII was isolated by PCR using specific primers derived from the sequence of M13 (Sambrook et al., 1989, Molecular Cloning: A Laboratory Manual, Cold Spring Harbor, N.Y.) and cloned into the EcoRI-NotI site of the modified Bluescript vector to generate the plasmid pMARS8 (FIG. 1). The Fv fragment ($V_L$-linker-$V_H$) generated as described below, was inserted into pMARS8 between the XbaI and the EcoRI site.

Example 2
Amplification of HIV-1 Ig heavy and light chains

Peripheral blood lymphocytes (PBL) were isolated from an asymptomatic HIV-1-seropositive mother who had high serum neutralizing titers to HIV-1 and did not transmit HIV-1 infection to her child during pregnancy. Peripheral blood mononuclear cells (PBMC) were isolated by Ficoll-Hypaque discontinuous gradient centrifugation. Total cellular RNA was isolated using the RNAzol kit (Cinna/Brotex Labs Inc., Houston, Tex., USA) according to the manufacturer's instructions. A total of 10 μg RNA in 12 μl of diethylpyrocarbonate (DEPC) water was utilized to synthesize cDNA using random hexamers as primers by reverse transcription as described (Williams et al., 1993, Transgene 1:1–11).

Figure 3:
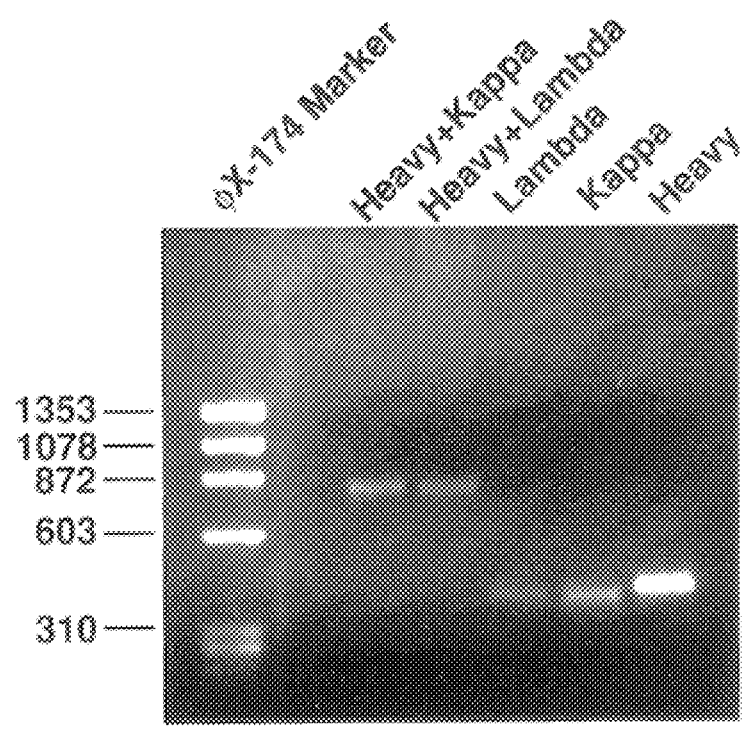

For PCR amplification of heavy and light chains, the oligonucleotide primers shown in FIG. 2 were used. The position of these primers relative to the sense strand of IgG cDNA is also shown in FIG. 2. The PCR cocktail (100 μl total volume) consisted of 16 μl deoxynucleoside triphosphate (dNTP; Boehringer, Mannheim, Germany; final concentration, 200 μM in each dNTP), 10 μl 10× PCR buffer (Perkin-Elmer Cetus Corp., Norwalk, Conn., USA), 0.2 μg/ml final concentration of oligonucleotide primers, 58.5 μl $H_2O$, 5 μl cDNA, and 1.2 units Taq polymerase (Perkin-Elmer Cetus Corp.). Amplification was carried out in a programmable thermal cycler (MJ Research, Watertown, Mass., USA) for 30 cycles. Each cycle included three steps: 94° C. for 30 sec; 48° C. for 1 minutes; and 72° C. for 2 minutes; finishing with 72° C. for 10 minutes. Positive amplification was assessed by agarose gel electrophoresis of PCR products (FIG. 3).

The oligonucleotide primers for amplification of kappa and heavy chains were chosen based on conserved DNA sequences found in the framework I (FRI) region of the variable regions and the CHI regions. The 3' primer of the kappa chains and the 5' primer of the heavy chains were designed with linker sequences based on earlier published work (Cabat et al., 1987, Sequences of Proteins of Immunological Interest, Bethesda: U.S. Department of health and Human Services). The linker sequences facilitate combination of the light and kappa chains by recombinant PCR. When kappa and heavy chains were amplified, a product of approximately 400 base pairs was evident and when recombinant PCR was performed, a product of approximately 800 base pairs was evident (FIG. 3).

Example 3
Generation Of $V_L$-linker-$V_E$ fragments by recombinant PCR

The $V_L$ and $V_H$ fragments from the first PCR reaction were separately isolated and purified on 2% low-melting agarose gel and purified by the standard phenol-chloroform extraction method (Sambrook et al., 1989, Molecular Cloning, A Laboratory Manual, Cold Spring Harbor, N.Y.). The Fv fragment of light and heavy chains were combined in a second recombinant PCR reaction. In this reaction, the 3' primer of light chains and the 5' primer of heavy chains were designed to contain the linker sequences described by Bird et al. (1988, Science 242:423–426) (FIG. 2). Recombinant PCR was performed using the splicing by overlap extension (SOE) method. Equal amounts of purified heavy and light chain DNA fragments from the first PCR reaction were mixed and used as templates. The oligonucleotide primers from the 5' side of the light and the 3' side of the heavy chain were used at 1/10th concentration of that used in the first PCR reaction. The reaction was initially conducted for five cycles using standard reaction conditions except that the primers were not added. Each cycle included three steps: 94° C. for 1 minutes, 58° C. for 1.5 minutes, and 72° C. for 2 minutes. The reaction was cooled to 4° C., followed by the addition of primers. The reaction was then continued for another 25 cycles at 94° C. for 1 minutes, 58° C. for 1.5 minutes, and 72° C. for 2 minutes, finishing with 72° C. for 10 minutes. Positive amplification was assessed by agarose gel electrophoresis of the PCR products (FIG. 3).

Example 4
Library Construction and Affinity Selection of Recombinant Clones by Panning The second PCR reaction products were digested with 50 mg/ml proteinase K and 0.5% sodium dodecylsulfate (SDS) for 30 minutes at 37° C. followed by a phenol-chloroform extraction and ethanol precipitation (crowe et al., 1991, Nucl. Acids. Res. 19:184). Recovered DNA was then digested with EcoRI and XbaI for 2 h at 37° C. and subjected to agarose gel electrophoresis. The DNA fragment was purified on a 2% low-melting temperature agarose gel and extracted with phenol-chloroform. This XbaI and EcoRI digested DNA was used directly for cloning. Similarly, the vector DNA was also digested with XbaI and EcoRI and was treated with calf intestinal alkaline phosphatase, and purified through a low-melting temperature agarose gel electrophoresis. Ligation was performed as per standard conditions and transformed into E. coli $DH_5aF'$ competent cells as described by the manufacturers (BRL, Gaithersburg, Md., USA). Following transformation, the library was constructed as described (Burton et al., 1991, Proc. Natl. Acad. Sci. USA 88:10134–10137).

Panning is a technique for rapid selection by which millions of clones can be screened at one time. The library was enriched for HIV-1 recombinant $gp120^{IIIB}$ binding, by panning three times as described (Burton et al., 1991, Proc. Natl. Acad. Sci. USA 88:10134–10137).

An IgG library expressing $V_L$-linker-$V_H$ was prepared from an HIV-1-asymptomatic mother. Heavy and kappa fragments were used for the construction of the library. The library initially yielded $1.9 \times 10^6$ recombinant clones. The phage surface expression library so made was expanded and panned against HIV-$1_{IIIB}$ recombinant gp120 coated on ELISA wells. Three rounds of panning were performed to enrich recombinant clones for gp120 binding. The enrichment process was monitored by titration after each round of panning. Initially, $1 \times 10^{11}$ colony forming units (CFU) was used for panning. After the first panning $2 \times 10^5$ was recovered, followed by $8 \times 10^6$ and $1 \times 10^8$ from the second and third round, respectively. The high number of CFU recovered at the end of the third panning indicates that the library was enriched for binding to HIV-$1_{IIIB}$ gp120.

Example 5
Analysis of soluble Fv for expression of proteins and screening of individual recombinant clones Phagemid clones from each round of panning were grown in 10 ml super broth (Burton et al., 1991, Proc. Natl. Acad. Sci. USA 88:10134–10137) containing 60 μg/ml ampicillin at 37° C. until an optical density (600 nm) of 0.4 was achieved. Isopropyl β-D-thiogalactopyranoside (1 mM) was added and the culture was grown overnight at 37° C. Cells were pelleted by centrifugation at 4000 rpm for 15 minutes at 4° C. and resuspended in 1.5 ml lysis buffer (1M NaCl, 50 mM Tris-HCI, pH 7.5, 0.1% Triton x-100, 1 mM phenylmethylsufanyl fluoride) and sonicated, for 2 minutes in ice and centrifuged at 4° C. in a microfuge for 15 minutes. The supernatant was collected and stored at −20° C., and analyzed by Western blotting for the expression of Fv fragments as described (Crowe et al., 1991, Nucl. Acids Res. 19:184). The concentration of Fv present in the bacterial supernatants were measured by ELISA using purified human antigen-binding fragments as standards.

Figure 5:
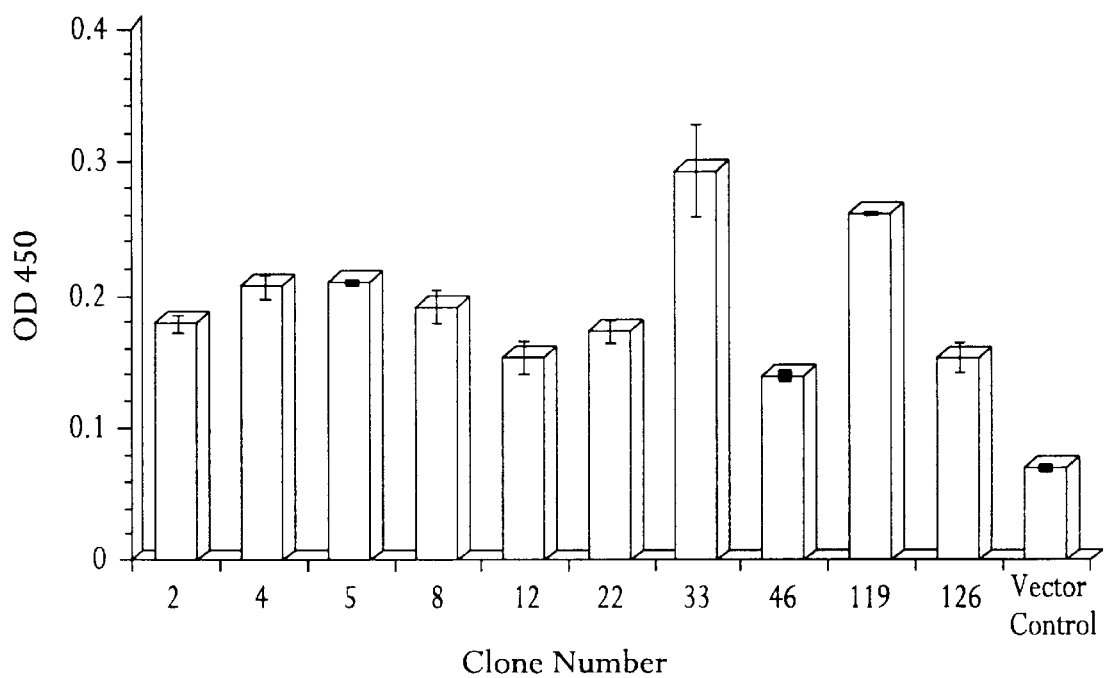

Individual clones from the third round of panning were grown, soluble Fv proteins were generated as described herein and the lysates were screened for HIV-1 recombinant gp120$_{IIIB}$ binding by ELISA. Briefly, the ELISA wells were coated with 50 µl antigen (HIV-1 gp120 at a concentration of 2 µg/ml) in 0.1M bicarbonate buffer overnight at 4° C. The assay was continued as described (Wand et al., 1993, AIDS Res. Hum. Retroviruses 9:849–859) and the results are shown in FIG. 5. HIV-1-seropositive serum was used as a positive control and vector without insert served as a negative control.

Figure 4:
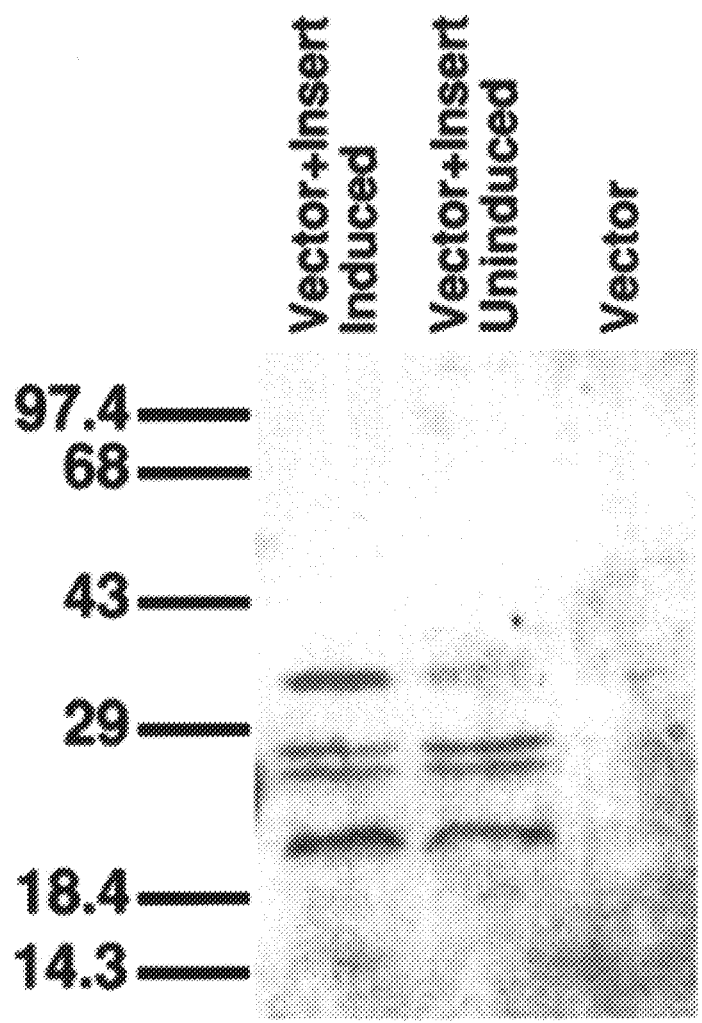

Initially, the soluble Fv from the entire library was analyzed for the expression of proteins by Western blotting (FIG. 4). It was observed that a band appeared clearly around 37 kD that did not appear in the lane containing vector alone. Following selection, 200 individual clones from the third panning were screened against HIV-1 gp120$_{IIIB}$ to select positive binders in ELISA analysis (FIG. 5). Several clones specifically bound gp120 compared with the vector control (FIG. 5). Some of the clones bound poorly to gp120; this may be due either to low amount of Fv expressed or to a low affinity of the Fv for the target molecule. It was observed that about 80% of the clones from the third panning were positive for HIV-1 gP120 binding.

Example 6

Mapping of recombinant clones using vaccinia constructs expressing different regions of HIV-1 gp120

In order to isolate a panel of antibodies having different binding patterns and functions, gross mapping was performed using vaccinia virus mutants expressing unique deletions of HIV envelope proteins (Wang et al., 1993, Proc. Natl. Acad. Sci. USA 90:4156–4160). The vaccinia virus constructs used in this analysis are described below. The amino-acid (aa) numbers are the total number of residues in the expressed proteins and truncations were made from the carboxyl terminus of the native gp160. VPE$_8$ (502 aa) expresses the entire gp120 molecule; VPE$_{20}$ (393 aa) expresses a gp120 molecule absent the carboxyl terminus and the CD4 binding region; VPE$_{21}$ (287 aa) expresses the gp120 molecule absent the carboxyl terminus, the CD4 binding region, and the V3 loop. VPE$_{22}$ (204 aa) expresses the first 204 aa of gp120. Vaccinia virus infected cell lysates were prepared from each mutant as described (Earl et al., 1991, J. Virol. 65:31–41). Each lysate was used as a source of antigen for mapping recombinant clones. Mapping was performed in an ELISA format as described herein.

Figure 6:
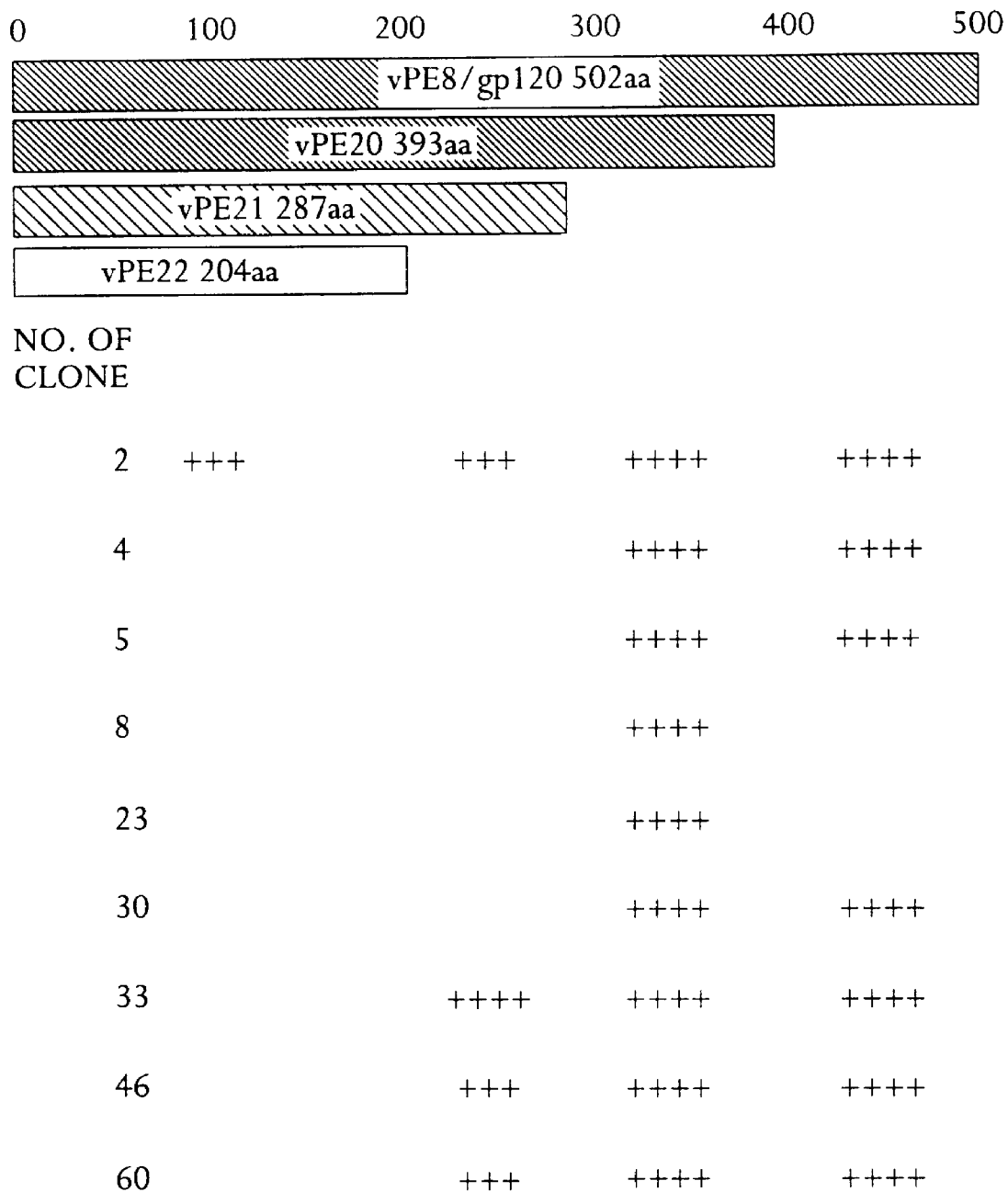

As noted above, representative clones which bound strongly to HIV-1 gp120 were mapped using vaccinia constructs expressing different gp120 deletion mutant proteins (FIG. 6). Four binding patterns were observed: clone 2 bound to all the constructs, suggesting a binding site on the amino terminal site of gp120; clones 33, 46, and 60 bound to aa 204–287; clones 4, 5, and 30 map to aa 287–393, which include the V3 loop; clones 8 and 23 bound to aa 398–400. Interestingly, clones 8 and 23 bind only to VPE$_{20}$ and not to VPE$_8$ which express a larger protein. This may be due to the masking of a binding site(s) in VPE$_8$ by the carboxyl termini of gp120, which are revealed on the shorter VPE$_{20}$ protein.

In summary these different binding patterns may indicate different biological activities of the antibodies.

Example 7

Virus neutralization assay

The soluble Fv supernatants obtained from representative clones at concentrations of 0.2–1.0–1.0 µg/ml were initially passed through Extracti-Gel (Pierce, Rockford, Ill., USA), a detergent-removing gel which removes Triton x-100 from the supernatants. The affinity separation of Fv supernatants from Triton x-100 was carried out as per the manufacturer's instructions. The detergent-free supernatant was filtered and used for the neutralization assays. Neutralization assays were performed as described (Nara, 1989, In: Techniques in HIV Research, Aldovini and Walker, eds. pp. 77–86), except that MT-2 cells were used as targets (Montifiori et al., 1988, J. Clin. Microbiol. 6:231–235). Specifically, 50 µl serial dilutions of Fv supernatants were mixed with 50 µl HIV-$_{IIIB}$ cell-free virus having a titer of 100 median tissue culture infective dose (TCID$_{50}$)/ml in a 96-well microliter plate. The virus serum mixture was incubated at 37° C. for 90 minutes. At the end of the incubation period, MT-2 cells in log phase were washed, counted and the cell suspension was diluted contain to 0.4×10$^6$ cells/ml; 100 µl of this cell suspension was then added to each well in the aforementioned plate. The plate was incubated further at 37° C. for 1 h. Cells were washed twice and suspended in 200 µl the medium containing 10% fetal bovine serum. Cell and virus controls were included in each assay. The plates were incubated at 37° C. in a CO$_2$ incubator. Following 3 days of incubation, the number of syncytia were counted in each well and the V$_n$/V$_0$ ratio and the percent of neutralization of HIV-1 was assessed (Nara, 1989, In: Techniques in HIV Research, Aldovini and Walker, eds. pp. 77–86; Montifiori et al., 1988, J. Clin. Microbiol. 6:231–235).

The representative clones which bound to HIV-1 gp120 were analyzed for their ability to neutralize HIV-1$_{IIIB}$ cell-free virus (FIGS. 7A–7J). The neutralization kinetics were determined by quantitation of the number of syncytia in tested wells versus virus control wells (V$_n$/V$_0$) using serial dilutions of bacterial lysates (Nara, 1989, In: Techniques in HIV Research, Aldovini et al., eds, NY, Stockton, pp 77–86). MT-2 cells infected with cell-free HIV-1$_{IIIB}$ that had been preincubated with lysates derived from vector alone readily formed syncytia. Out of 10 clones tested, at least five exhibited good neutralizing activity (60–75% neutralization). Other clones, even though they bound to HIV-1 gp120 very efficiently, did not neutralize the virus. These results support other studies which suggest that the location on gp120 to which the antibody binds rather than the binding affinity governs the neutralization phenotype of the antibody.

Example 8

Nucleic acid sequencing

Nucleic acid sequencing of representative clones was carried out on a 373A automated DNA sequencer (Applied Biosystems Inc., Foster City, Calif., USA) using Taq fluorescent dideoxynucleotide terminator cycle sequencing kit (Applied Biosystems). Primers for the elucidation of kappa chain sequence were as follows: 5'-TTATTACTCGCTGCCCAACCAGCG-3' [SEQ ID NO:21] hybridizing to the positive strand and light chain linker primer 5'CTGATAAGATTTAGATTC-3' [SEQ ID NO:22] hybridizing to the negative strand. The heavy chain was sequenced using the heavy-chain linker sequences (5'-GGCTCCGAA-TCTAAATCTTATCAG-3') [SEQ ID NO:23] hybridizing to the positive strand, and gene VIII sequence primer (5'AAAGGCCGCTT-TTGCGGGATCGTC-3') [SEQ ID NO:24] hybridizing to the negative strand, respectively.

FIG. 8 depicts a comparison of the segments of heavy chains of different clones. This comparison reveals that the panel of antibodies which were cloned are very diverse. Further, the Fv which were generated fall within group II heavy-chain antibodies (Cabat et al., 1987, Sequences of Proteins of Immunological Interest, Bethesda: U.S. Department of health and Human Services). It is clear from sequence data that clone 46 and clone 119 comprise similar D/J regions suggesting clonal relatedness therebetween. The other two clones had distinct D/J regions, indicating that they arose from separate precursors.

The data presented herein establish that the methods of the invention are simple and effective for the expression of Fv antibody genes in vitro. Single-chain Fv antibodies for HIV-1 may be useful for several reasons including their smaller size; the fact that they may expose antigen-binding sites potentially more efficiently; and the fact that high levels of expression of single chain Fv may be achieved by using phage surface expression vectors. Such recombinant molecules possess traditional antibody-based biological activities which are extremely valuable as investigational reagents and may give important insight into natural immunity.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A recombinant single chain antibody molecule selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19 and SEQ ID NO:20.

2. An isolated DNA encoding the recombinant single chain antibody molecule of claim 1.

3. A method of treating a human infected with Human Immunodeficiency Virus type 1 (HIV-1) comprising administering to said human a recombinant single chain antibody molecule selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO: 13, SEQ ID NO:14, SEQ ID NO:15, SEQ ID NO:16, SEQ ID NO:17, SEQ ID NO:18, SEQ ID NO:19 and SEQ ID NO:20.

4. The vector, pMARS8.

5. A method of treating a human infected with Human Immunodeficiency Virus comprising administering to said human a pharmaceutical composition that consists essentially of a virus neutralizing recombinant single chain antibody molecule selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO: 12, SEQ ID NO:13, SEQ ID NO:14, SEQ ID NO:15, SEQ ID NO:16, SEQ ID NO:17, SEQ ID NO:18, SEQ ID NO:19 and SEQ ID NO:20 providing passive inmunity.

* * * * *